(12) United States Patent
Nielsen et al.

(10) Patent No.: US 8,728,508 B2
(45) Date of Patent: May 20, 2014

(54) HYDROPHILIC COATING AND A METHOD FOR THE PREPARATION THEREOF

(75) Inventors: Bo Rud Nielsen, Allerod (DK); Niels Jorgen Madsen, Allerod (DK)

(73) Assignee: Coloplast A/S, Humlebaek (DK)

( * ) Notice: Subject to any disclaimer, the term of this patent is extended or adjusted under 35 U.S.C. 154(b) by 1148 days.

(21) Appl. No.: 10/540,108

(22) PCT Filed: Dec. 19, 2003

(86) PCT No.: PCT/DK03/00927
§ 371 (c)(1),
(2), (4) Date: Jun. 26, 2006

(87) PCT Pub. No.: WO2004/056909
PCT Pub. Date: Jul. 8, 2004

(65) Prior Publication Data
US 2006/0251694 A1    Nov. 9, 2006

(30) Foreign Application Priority Data

Dec. 20, 2002   (DK) .................................. 2002 01970

(51) Int. Cl.
*A61K 6/083* (2006.01)
*A61F 13/00* (2006.01)
*B05D 3/02* (2006.01)

(52) U.S. Cl.
USPC .......................................... 424/422; 427/2.26

(58) Field of Classification Search
USPC ......................................... 424/422; 427/2.26
See application file for complete search history.

(56) References Cited

U.S. PATENT DOCUMENTS

| 4,373,009 A | 2/1983 | Winn |
| 4,876,126 A | 10/1989 | Takemura et al. |
| 5,001,009 A | 3/1991 | Whitbourne |
| 5,005,287 A | 4/1991 | Ritter |
| 5,006,407 A | 4/1991 | Malhotra |
| 5,431,916 A | 7/1995 | White |
| 5,484,565 A * | 1/1996 | Larsen et al. ................. 264/230 |
| 5,688,855 A | 11/1997 | Stoy et al. |
| 2002/0037943 A1* | 3/2002 | Madsen .......................... 522/86 |
| 2002/0045049 A1 | 4/2002 | Madsen |
| 2004/0043052 A1* | 3/2004 | Hunter et al. ................. 424/426 |

FOREIGN PATENT DOCUMENTS

| EP | 0 166 998 | 1/1986 |
| EP | 0 289 996 | 11/1988 |
| EP | 0 570 370 B1 | 11/1993 |
| EP | 0 991 702 B1 | 4/2000 |
| JP | 3-503379 | 8/1991 |
| WO | 89/09246 | 10/1989 |
| WO | WO 89/09246 * | 10/1989 ............... C09D 3/00 |
| WO | WO 90/05162 | 5/1990 |
| WO | WO 98/58990 | 12/1998 |
| WO | WO 99/01129 | 1/1999 |

OTHER PUBLICATIONS

Fan, Y.L., et al., "Hydrophilic Lubricious Coatings for Medical Applications," Chem., Polym. Material Science Engineering, No. 63, pp. 709-716, (1990).

* cited by examiner

*Primary Examiner* — Dennis Heyer
(74) *Attorney, Agent, or Firm* — Coloplast Corp., Coloplast A/S; Nick Baumann

(57) ABSTRACT

The present invention provides a method for the preparation of a cross-linked hydrophilic coating of a hydrophilic polymer on a substrate polymer surface of a medical device, involving the use of a polymer solution comprising 1-20% by weight of a hydrophilic polymer, 0-5% by weight of additive(s), and the balance of a vehicle with plasticizing effect on the hydrophilic polymer, wherein the vehicle comprises at least one plasticizer having a solubility in water of at least 6 g/L, a boiling point above 210° C. at 760 mmHg, and Hansen $\delta_H$ parameter of less than 20. Furthermore, the invention provides a medical device, e.g. a catheter or guide wire, provided with such a hydrophilic coating. The invention also provides the use of specific polymer solution for the preparation of a cross-linked hydrophilic coating.

23 Claims, No Drawings

HYDROPHILIC COATING AND A METHOD FOR THE PREPARATION THEREOF

This is a nationalization of PCT/DK03/000927 filed Dec. 19, 2003 and published in English.

FIELD OF THE INVENTION

The present invention relates to a medical device carrying a cross-linked hydrophilic coating. Furthermore, the invention relates to a method for preparing a cross-linked hydrophilic coating on the substrate polymer surface of a medical device. The present invention also relates to the use of a specific polymer solution for the preparation of a cross-linked hydrophilic coating.

A hydrophilic coating according to the invention may be used for coating the surface or a part thereof of a wide range of products in order to provide low friction properties to a surface. As examples of products which may be provided with a surface having a low friction when wet are medical instruments and devices such as catheters, endoscopes and laryngoscopes, tubes for feeding or drainage or endotracheal use, guide wires, condoms, barrier coatings, e.g. for gloves, wound dressings, contact lenses, implants, extracorporeal blood conduits, membranes e.g. for dialysis, blood filters, devices for circulatory assistance or non-medical products such as packaging for foodstuff, razor blades, fishermen's net, conduits for wiring, water pipes having a coating inside, water slides, sports articles, cosmetic additives, mould release agents, and fishing lines and nets.

BACKGROUND OF THE INVENTION

The application of hydrophilic coatings on medical devices has become a very important method to improve biocompatibility between living tissue and the medical device. Another important property of hydrophilic coatings is to reduce the friction and to render biomedical devices slippery when wet. Medical devices like catheters, guide wires, endoscopes etc. are often sliding in direct contact with the surface of living tissue when in use. Catheters and guide wires may e.g. be introduced into the blood vessels or a catheter for catheterisation of the bladder is introduced through the urethra and withdrawn later after emptying the bladder when performing catheterisation or after some time when performing more or less permanent catheterisation. In both applications, the medical device is sliding in direct contact with a physiological surface, the walls of the blood vessels, or the mucosa of the urethra, respectively.

In order to reduce or avoid the risks of health and discomfort like inflammatory damage and degeneration caused by the medical device, hydrophilic coatings having very low friction coefficient when wet have been applied to the surface of the medical devices. Hydrophilic coatings having a low friction coefficient when wet typically comprise hydrophilic polymers such as polyvinyl pyrrolidone (PVP), polycarboxylic acids, esters, salts and amides of poly(meth)acrylic acid, copolymers of poly(methyl vinyl ether/maleic anhydride) and polyglycols like polyethyleneglycol (PEG).

According to Y. Fan (in Fan Y. L. 1990: "Hydrophilic Lubricious Coatings for Medical Applications", Amer. Chem., Polym. Mater. Sci. Eng., 63:709-716.), the methods described in the patent literature by which hydrophilic coatings can be applied onto a substrate can be roughly divided into 5 different methods:
(1) Simple coating with hydrophilic polymers,
(2) Blending or complexing of hydrophilic polymers,
(3) Formation of interpenetrating polymeric networks,
(4) Coating with chemically reactive hydrophilic polymers and
(5) Surface grafting of hydrophilic monomers.

The first three types of hydrophilic coatings have several disadvantages: they have low abrasion resistance giving the devices a short effective lifetime. A considerable amount of polymeric residuals is released at the site where it is introduced and at the same time, this loss of polymeric material rapidly increases the friction coefficient. This abrasion or dissolution may even be so pronounced that the reduction of the friction is not effective during all of the service period of the medical device and the low friction may even have vanished when the device is to be retracted.

The fourth method involves the use of chemically reactive hydrophilic polymers that are chemically bonded to substrates or primers containing e.g. aldehyde, epoxy or isocyanate groups. The fourth coating method suffers from the drawback of the use of toxic reactive materials and in order to avoid a residual toxic effect there is a demand of long reaction times and eventually washing steps in the process. U.S. Pat. No. 4,373,009 discloses that a hydrophilic layer is formed on a substrate, e.g. wound drains, catheters, surgical tools and arterlovenous shunts, by binding unreacted isocyanate groups on the substrate surface and treating the surface with a hydrophilic copolymer made from vinyl-pyrrolidone monomers and monomers containing an active hydrogen adapted to form covalent bonds with the isocyanate.

EP 0 166 998 B1 discloses a medical instrument having a surface with a reactive functional group covalently bonded to a water-soluble polymer of a cellulose polymer, maleic anhydride polymer, polyacrylamide or a water-soluble nylon or nylon derivative and having lubricity when wetted. The substrate is treated with a solution of a compound containing the reactive functional group so that an undercoat is formed which contains this group. The undercoat is then coated with the water-soluble polymer that bonds to the functional group.

EP 0 289 996 A2 discloses a method for forming and applying a hydrophilic coating to a moulding (e.g. a razor blade), in which process a solution containing a water-soluble polymer, more particularly polyvinyl pyrrolidone or a copolymer thereof, one or more radically polymerisable vinyl monomers and a photo initiator is applied to the moulding and the applied solution is exposed to an UV radiation for curing purposes.

EP 0 991 702 A1 discloses a coating for medical devices, said coating comprising UV-radiation cross-linked hydrophilic polymer and which coating further comprises a water soluble compound like glucose, sorbitol, halides, acetates, citrates, benzoates of alkali metals or alkaline earth metals or silver, glycerine or urea.

EP 0 570 370 B1 discloses a composition for a hydrophilic coating said composition comprising a hydrophilic polymer selected from the group of polyvinyl pyrrolidone, polyvinyl pyrrolidone-polyvinyl acetate copolymer, a mixture thereof and a water-insoluble stabilizing polymer selected from the group of polymethyl vinyl ether or maleic anhydride, an ester of a copolymer, and nylon and a mixture thereof said composition being substantially more slippery when wet than when dry. Furthermore, such disclosed compositions comprise a plasticizing agent such agent preferably being selected from the group consisting of camphor, polyvinyl butyral, dibutyl phthalate, castor oil, dioctyl phthalate, acetyl tributyl citrate, dibutyl sebacate, sebacic acid and alkyl resin.

Thus, there are a number of ways to achieve hydrophilic coatings for medical devices either based on coating with two layer systems where the first layer serves as a base layer or by coating with single layer system where covalent bonding to substrate and polymer cross-linking are used for achieving coating strength. Hydrophilic coatings as described in the cited patents or patent applications tend to be brittle when dry with lack of resistance to material stresses. Cracks in the coating or horizontal debonding from the substrate are often experienced complications for such coatings. This might be overcome for non cross-linked coatings by using the teaching of EP 0 570 370 B1.

It has, however, been found that using plasticizers according to the teaching from EP 0 570 370 B1 in coatings based on hydrophilic cross-linked polymers will not result in high bonding strength and coating integrity. Neither does the use of highly hydrogen bonding, hydrophilic plasticizers like glycerine and diethylene glycol result in sufficient coating integrity nor bonding strength.

WO 90/05162 discloses an article having a two-phase surface coating of low friction when wetted. The coating consists of polyurethane and poly(N-vinyl lactam) where the poly(N-vinyl lactam) primarily forms the inner phase and the polyurethane primarily forms the outer phase. The coating is formed by application of a solution comprising the polyurethane and the poly(N-vinyl lactam) in combination with a mixture of solvents of which the poly(N-vinyl lactam) is only partly soluble in the least volatile solvent. Subsequent curing of the coating is not mentioned or indicated.

U.S. Pat. No. 5,688,855 discloses a hydrophilic coating composition comprising a mixture of a hydrogel-forming polymeric component and a polymeric water-soluble component in a solvent for dissolving both polymeric components.

Thus, there is still a need for improved hydrophilic coatings as well as for simplified procedures for the preparation of hydrophilic coatings.

BRIEF DESCRIPTION OF THE INVENTION

In view of the prior art, there is still a need for alternative or even improved stable and lubricious coatings for medical devices, and improved methods for preparing such coatings on medical devices.

The present invention solves the problem by providing the method that features a group of plasticizers with fair water solubility, high boiling point and small to medium hydrogen bonding ability, and which provides cross-linked coatings that are stable and lubricious when wet.

The invention thus relates to a method for preparing a cross-linked hydrophilic coating on a substrate polymer surface of a medical device, cf. claim 1, which provides a hydrophilic coating showing high abrasion resistance and low friction coefficient when wet.

The invention also relates to a medical device carrying a cross-linked hydrophilic coating, cf. claims 7 and 8, which exhibits high abrasion resistance and low friction coefficients when wet.

The invention further relates to the use of a polymer solution for the preparation of a cross-linked hydrophilic coating, cf. claim 10.

DETAILED DESCRIPTION OF THE INVENTION

The present invention is based on the finding that the preparation of cross-linked hydrophilic coatings using one or more particularly selected plasticizers provides advantageous properties to said coatings and simplifies the manufacturing process.

Thus, the present invention provides a method for the preparation of a cross-linked hydrophilic coating of a hydrophilic polymer on a substrate polymer surface of a medical device, said method comprising the steps of:
(i) providing a medical device comprising a substrate polymer having the substrate polymer surface,
(ii) providing a polymer solution comprising 1-20% by weight of a hydrophilic polymer, 0-5% by weight of additive(s), and the balance of a vehicle with plasticizing effect on the hydrophilic polymer, said vehicle comprising at least one plasticizer having a solubility in water of at least 6 g/L, a boiling point above 210° C. at 760 mmHg, and a Hansen $\delta_H$ parameter of less than 20,
(iii) applying said polymer solution to said substrate polymer surface,
(iv) evaporating at least a part of the vehicle from said polymer solution present on said substrate polymer surface, and curing said hydrophilic polymer.

Substrate Polymer

Basically, the coating according to the invention may be applied to any type of substrate. However, for the bonding of the coating, it will be important that the vehicle will be able to plasticize the very surface of the substrate for improving the polymer chain interaction. This means that the coating according to the invention will be especially useful in the case of substrate polymers such as polyurethanes and copolymers thereof, or polyether block amides such as Pebax™ or other polymer materials including polyvinyl chloride, polyamide, silicone, styrene-ethylene/butylene-styrene block copolymers (SEBS), styrene-isoprene-styrene block copolymers (SIS), styrene-ethylene/propylene-styrene block copolymers (SEPS), ethylene-vinyl acetate copolymers (EVA), polyethylene (PE), metallocene-catalyzed polyethylene, and copolymers of ethylene and propylene or mixtures of such. For some of the combinations of substrate polymers and hydrophilic coatings, a primer coating may advantageously be applied before application of the polymer solution. In some embodiments, the primer coating may be prepared from a dilute solution of the polymer solution.

It is believed that highly plasticized polymeric materials like soft PVC will be less useful as substrates as the fairly hydrophobic plasticizers of such materials tend to migrate into the coating and reduce the wettability of the coating as well as to interfere with the cross-linking reaction, especially when the drying period after the application of the polymer solution (e.g. dipping of the substrate polymer (the device)) is long. However, thin primer coatings of soft PVC contain too little amount of hydrophobic plasticizer to interfere with the coating according to the invention and may in fact be quite useful in connection with certain substrates.

The substrate polymer onto which the coating is applied is, however, preferably non-plasticized.

The surface on which the hydrophilic coating is applied may be the full surface of the substrate polymer or a partial surface. Alternatively, a part of the surface may be masked with a film or the like so as to form a predetermined pattern of the hydrophilic coating on the surface.

Polymer Solution

Typical examples of the hydrophilic polymer are polyvinyl pyrrolidone, polyvinyl alcohol, poly(meth)acrylic acid, poly(meth)acrylic amides, polyethylene glycol, carboxymethylcellulose, cellulose acetate, cellulose acetate propionate, chitosan, polysaccharides, or any homopolymer or copolymer of two or more of the monomers, N-vinyl pyrrolidone, vinyl alcohol, (meth)acrylic acid, (meth)acrylic amides, (meth)acrylic esters such as hydroxyethyl methacrylate, maleic anhydride, maleimide, methyl vinyl ether, alkyl vinyl ethers with vinylic side chains, and other unsaturated compounds. Furthermore, the hydrophilic polymer may be any blend of these homopolymers or copolymers. Other radiation curing hydrophilic polymers comprising unsaturated vinylic double bonds can also suitably be used for the coating. Such polymers may be achieved by copolymerising into a prepolymer an acrylic substance like dimethylaminoethylmethacrylate with N-vinyl pyrrolidone, methacrylic acid, methacrylic esters, methyl vinyl ether etc. Such a prepolymer is typically coated to the surface and ultimately radiation cured. The hydrophilic polymer of the coating may further be achieved by adding monomers of acrylic nature to the above-mentioned types of polymers.

Alternatively, hydrophilic polymers containing active hydrogens capable of reacting with isocyanate groups may be used in urethane type coatings. This is achieved by first coating an isocyanate compound onto the substrate polymer surface where such coating either adheres or covalently bonds to reactive groups at the surface. Secondly, a hydrophilic, reactive polymer is coated on top of such dried coating containing isocyanate groups. Said polymers may contain —OH, —SH, —NH—, —NH$_2$ and —CONH$_2$ groups. The polymers may be acrylic polymers and copolymers comprising acrylamide, hydroxyethyl acrylate, acrylic acid, polyethylene glycol methacrylate, polypropylene glycol methacrylate and the like.

Furthermore, polyethylene glycols and polyvinyl pyrrolidone are useful for such hydrophilic coatings.

The hydrophilic polymer of the coating is preferably selected from the group of polyvinyl pyrrolidone or copolymers thereof, e.g. polyvinyl pyrrolidone-vinyl acetate copolymers. These types of polymers are very useful for cross-linking by radiation.

When using the pure polyvinyl pyrrolidone (poly(N-vinyl-2-pyrrolidone); PVP), various chain lengths may be selected each giving various characteristics to the coating. Typically, such polyvinyl pyrrolidone polymers have a number average molecular weight of above 100,000. As an example, PVP K-90 with 1,200,000 in MW can be selected but other types of PVP with other molecular weights may also be used.

The hydrophilic polymer(s) constitute(s) 1-20%, preferably 2-15%, such as 3-10%, by weight of the polymer solution.

The choice of vehicle and in particular the plasticizer(s) for the method of the invention is of utmost importance. Certain requirements are to be set for the vehicle in order for it to sufficiently plasticize the hydrophilic polymer that forms the hydrophilic coating after drying.

A number of plasticizers have previously been described for use in hydrophilic coating materials for biomedical applications or in other devices. Examples of such are camphor, polyvinyl butyral, and dibutyl phthalate, castor oil, dioctyl phthalate, acetyl tributyl citrate, and dibutyl sebacate, sebacic acid and alkyl resin. When using such plasticizers in coatings, two undesirable properties are achieved. Owing to the hydrophobic nature of the plasticizers, the resulting coatings tend to show water repellent character in the initial swelling period when in contact with an aqueous swelling media. This retards the quick formation of for instance low friction which is an important feature for medical devices introduced in the body like catheters or guide wires. Secondly, the hydrophobic plasticizers are reducing the capability of cross-linking, in the sense of internal cohesion and bonding to substrate, leaving only weak coatings with low abrasion resistance when swollen.

Plasticizers ordinarily used for hydrogels are strongly hydrogen bonded, like glycerol or diethylene glycol. Such plasticizers will, when used for plasticizing the coating, in a similar way reduce coherence and abrasion strength of the resulting coating.

The inventors have now found that some plasticizers appear to work in a different manner. These do not interfere with the radical chemistry involved in the cross-linking reaction of the hydrophilic polymer for the coating and enable the bonding of the coating to the substrate. Furthermore, these do not retard water uptake in the coating when immersed in water before use. These plasticizers are among others triethyl citrate and glycerol diacetate. This type of plasticizers can be characterised by their high boiling point, their fair water solubility and their solubility parameters. The requirements are:

1. The boiling point at 760 mmHg or corrected to 760 mmHg must be greater than 210° C.
2. The solubility in water must be at least 6 g/L
3. The Hansen $\delta_H$ parameter must be smaller than 20

The boiling point may be determined at reduced pressure because decomposition of the plasticizer may take place at a lower temperature than the boiling point at 760 mmHg. A correction to boiling point at 760 mmHg may then be carried out with a standard pressure-temperature nomograph, which is e.g. available free of charge at the website of the Sigma-Aldrich chemical company.

In predicting the compatibility of polymer systems or blends a solubility approach may be used. The 'Hansen Solubility Parameter' theory is considered to be the most appropriate instrument for doing this. The theory is e.g. described in C. M. Hansen: "Hansen Solubility Parameters, A User's Handbook", CRC Press, Boca Raton, 1999. The basis is that the total energy of evaporation of a liquid consists of several individual parts. These arise from dispersion forces (atomic), permanent dipole—dipole forces (molecular) and hydrogen forces (electron exchange). Hence, the equations for the combined solubility expression is $\delta^2=\delta_D^2+\delta_P^2+\delta_H^2$. The individual D, P and H components of the equation may be plotted in a three dimensional diagram and spatial domains can be defined for the various categories of plasticizers. Similarly two of the components may be plotted against one another if the third does not influence the equation like for instance in case of non-existence of hydrogen bonding. In the current invention, apparently plasticizers with a high value of $\delta_H$, such as alcohols, glycols and carboxylic acids, solvate the coating polymer so strongly that the UV curing is impeded and a stable coating cannot be formed.

This being said, the particularly selected plasticizers each have a solubility in water of at least 6 g/L, a boiling point above 210° C. at 760 mmHg (atmospheric pressure), and a Hansen $\delta_H$ parameter of less than 20.

The value of $\delta_H$ is fairly critical and is often below 18, such as below 15.

The boiling point of the suitable plasticizer(s) is often above 225° C., e.g. above 250° C., such as above 265° C.

The water solubility of the suitable plasticizers is often greater than 50 g/L.

The preferred plasticizers are acetyl triethyl citrate, dimethyl sulfone, ethylene carbonate, glycerol diacetate, glycerol triacetate, hexamethylphosphoramide, isophorone, methyl salicylate, N-acetyl morpholine, propylene carbonate, quinoline, sulfolane, triethyl citrate, and triethyl phosphate. Particular examples are acetyl triethyl citrate, glycerol diacetate, glycerol triacetate, and triethyl citrate. The plasticizers may be used singly or in combination. The less toxic plasticizers are preferred. The relevant parameters of the preferred plasticizers are listed in Table 1.

TABLE 1

Parameters of preferred plasticizers

| Plasticiser | Delta D | Delta P | Delta H | Solubility in water (g/L) | Boiling point (Bp, deg. C.) | Bp corrected to 760 mm Hg |
|---|---|---|---|---|---|---|
| Acetyl triethyl citrate | 16.6 | 3.5 | 8.6 | 7.2 | 132/1 mm Hg | 320 |
| Dimethyl sulfone | 19 | 19.4 | 12.3 | Miscible | 238 | 238 |
| Ethylene carbonate | 19.4 | 21.7 | 5.1 | Miscible | 248 | 248 |
| Glycerol diacetate | 16.4 | 8.9 | 14.2 | Miscible | 280 | 280 |
| Glycerol triacetate | 16.5 | 4.5 | 9.1 | 71 | 259 | 259 |
| Hexamethyl-phosphoramide | 18.5 | 8.6 | 11.3 | Miscible | 235 | 235 |
| Isophorone | 16.6 | 8.2 | 7.4 | 12 | 214 | 214 |
| Methyl salicylate | 16 | 8 | 12.3 | 7.4 | 233 | 233 |
| N-Acetyl morpholine | 18.3 | 5.3 | 7.8 | Miscible | 152/50 mm Hg | 245 |
| Propylene carbonate | 20 | 18 | 4.1 | 190 | 240 | 240 |
| Quinoline | 19.4 | 7 | 7.6 | 6 | 238 | 238 |
| Sulfolane (thiolane sulfone, tetra-methylene sulfone) | 18.4 | 16.6 | 7.4 | Miscible | 104/0.2 mm Hg | 310 |
| Triethyl citrate | 16.5 | 4.9 | 12 | 65 | 127/1 mm Hg | 312 |
| Triethyl phosphate | 16.7 | 11.4 | 9.2 | Miscible | 215 | 215 |

Without being bound to any specific theory, it is believed that the specified plasticizers act by improving the physical intermingling of the individual chains of the hydrophilic polymer of the coating in the interface between the substrate and the coating due to a balanced ability to swell the very surface of the substrate. Surprisingly, it appears that the plasticizers that fulfil the above criteria do not inhibit or radically reduce the ability to cross-link the coating by ultraviolet light.

The plasticizer(s) preferably constitute(s) 1-40%, such as 4-40%, e.g. 4-20%, such as 5-15%, by weight of the polymer solution.

This being said, the polymer solution typically comprises 1-20% by weight of the hydrophilic polymer, 0-5% by weight of additive(s), and the balance of the vehicle including the specified plasticizer(s).

Although the plasticizer as such may have solvent properties, the vehicle may comprise a solvent in addition to the plasticizer.

The solvent is to be understood in the normal sense, but should—in the present context—of course not include the plasticizers defined above. Thus in preferred embodiments, the vehicle comprises at least one solvent in addition to the at least one plasticizer. Any solvent can in principle be used for the vehicle. Especially preferred solvents include 1,3-dioxolane and other ethers, acetone and other ketones, dimethyl sulfoxide and other sulfoxides, dimethyl formamide and other amides, N-methyl-2-pyrrolidone and other lactams, ethanol and other alcohols, glycols, glycol ethers, glycol esters, other esters, amines, heterocyclic compounds, morpholine and derivatives, alkylated urea derivatives, liquid nitriles, nitroalkanes, haloalkanes, haloarenes, trialkyl phosphates, dialkyl alkanephosphonates, and other commonly known organic solvents. The preferred solvents may either be used singly or in combination. Currently preferred solvents are selected from ethanol, N-methyl-2-pyrrolidone, dimethyl sulfoxide, acetone, 1,3-dioxolane and dimethyl formamide.

The vehicle preferably comprises a volatile or fairly volatile solvent.

The terms "volatile solvent" and "fairly volatile solvent" should be seen in the light of the evaporation rate. For this purpose, the evaporation rate relative to butyl acetate is typically used to provide certain guidelines in this respect (see in particular A. Saarnak, C. M. Hansen: "Löslighedsparametrar, Karaktärisering av färgbindemedel och polymerer", publication from the Scandinavian Paint and Printing ink Research Institute, Hørsholm, Denmark, May 1982 (in Swedish)). According to this paper, the evaporation rate (ER) is "Fast" if it is more than 3.0 times greater than that of butyl acetate (ER=1.0), i.e. ER>3.0; "Medium" if 0.8<ER<3.0; "Slow" If 0.1<ER<0.8; and "Very slow" if ER<0.1. "Volatile" and "Fairly volatile" correspond to a "fast" and "medium" evaporation rate, respectively.

Volatile and fairly volatile solvents typically have a boiling point of up to 120° C. Examples of volatile and fairly volatile solvents are acetone, 1,3-dioxolane, ethanol, ethyl acetate, methanol, methyl ethyl ketone (2-butanone), tetrahydrofuran (THF), isobutanol (2-methyl-1-propanol), butyl acetate, isobutyl acetate, methyl isobutyl ketone (4-methyl-2-pentanone), 1-propanol, and 2-propanol.

In a preferred embodiment, the vehicle comprises at least one of ethanol, acetone, dimethyl formamide and 1,3-dioxolane, and at least one of N-methyl-2-pyrrolidone and dimethyl sulfoxide. In a particular embodiment, the vehicle comprises ethanol and N-methyl-2-pyrrolidone, or ethanol and dimethyl sulfoxide, or ethanol, N-methyl-2-pyrrolidone and dimethylsulfoxide. In another embodiment, the vehicle comprises acetone and N-methyl-2-pyrrolidone, or acetone and dimethyl sulfoxide, or acetone, N-methyl-2-pyrrolidone and dimethylsulfoxide.

Typically, the solvent(s) constitute(s) 50-95%, e.g. 60-90%, such as 70-85%, by weight of the polymer solution.

In one embodiment, the polymer solution consists of:
1-20% by weight of the hydrophilic polymer,
0-5% by weight of additive(s),
1-40% by weight of plasticizer(s), and
50-95% by weight of solvent(s).

In a preferred embodiment, the polymer solution consists of:
1-20% by weight of polyvinyl pyrrolidone as the hydrophilic polymer,
0-5% by weight of additive(s),
1-40% by weight of plasticizer(s) selected from acetyl triethyl citrate, dimethyl sulfone, ethylene carbonate, glycerol diacetate, glycerol triacetate, hexamethylphosphoramide, isophorone, methyl salicylate, N-acetyl morpholine, propylene carbonate, quinoline, sulfolane, triethyl citrate, and triethyl phosphate, and 50-95% by weight of solvents selected from ethanol, N-methyl-2-pyrrolidone, dimethyl sulfoxide, acetone, 1,3-dioxolane and dimethyl formamide.

In some interesting embodiments, the substrate polymer is polyurethane. In further interesting embodiments, the hydrophilic polymer is polyvinyl pyrrolidone. In particular, the substrate polymer is polyurethane and the hydrophilic polymer is polyvinyl pyrrolidone.

One or more additives may be included in the polymer solution, e.g. so as to facilitate the cross-linking of the hydrophilic polymer or so as to improve bonding of the polymer to the substrate surface. Such additives are known in the art and may include UV-initiators, e.g. as described in WO 98/58990. A suitable example of a UV-polymerisation initiator is Esacure® KIP 150. Furthermore, anti-infective agents could be included If desirable.

The Method Steps

The method of the invention provides a cross-linked hydrophilic coating of a hydrophilic polymer on a substrate polymer surface of a medical device. The method comprises the following steps (i)-(iv).

Step (i)

As mentioned above, the substrate polymer surface may be the native surface of a medical device, or may be surface treated so as to facilitate strong bonding of the hydrophilic coating to the substrate polymer. The surface of the substrate polymer may be the complete physical surface or a fraction thereof. For many medical devices, it is only necessary to coat the part of the substrate polymer surface that comes into direct contact with the surface of living tissue when in use. Thus, the step of providing a substrate polymer having the substrate polymer surface will be evident for the person skilled in the art.

Step (ii)

The selection of polymer solution is crucial for the method of the invention. The choice of hydrophilic polymer, vehicle including solvent(s) and plasticizer(s) and additives is described above. The solution may be prepared by mixing the components of the vehicle with the hydrophilic polymer in order to obtain the polymer solution. The mixing order is not particularly critical as long as a homogeneous (and possibly clear) solution is obtained. Thus, the step of actual preparation of the polymer solution will be evident for the person skilled in the art in view of the above directions with respect to choice of vehicle components.

Step (iii)

Application of the polymer solution to said substrate polymer surface is conducted following conventional methods such as dip coating, spray coating, application by means of brushes, rollers, etc., as will be evident for the person skilled in the art. With due consideration of the production process, it is preferred that the application of the polymer to the substrate polymer surface is performed by dipping the medical device (or the relevant surface thereof) into the polymer solution.

In a preferred embodiment, the polymer solution is applied to the substrate polymer surface In one single application step, such as in a one-dip process.

In another preferred embodiment, the polymer solution is applied to the substrate polymer surface in two or three individual application steps, in particular in two individual application steps, such as in a two-dip process.

The dipping process typically takes place by immersing the substrate in the polymer solution and then withdrawing them at a speed of 0.2-10 cm per second at a temperature of in the range of 0-100° C., such as at 1-2 cm per second at room temperature.

For all embodiments, it should be understood that the substrate polymer may be primed in one or more preceding step(s) and that such (a) preceding step(s) may be performed in addition to the before-mentioned application step(s) (e.g. one-dip process or two-dip process) of applying the polymer solution. As mentioned above, the primer coat may be formed from a dilute solution of the polymer solution.

Hence, in a preferred embodiment, the application of the polymer solution (one or two dips, In particular one dip) to the substrate polymer surface (step (iii)) is preceded by a priming step in which a dilute solution of the polymer solution (e.g. using a dilution factor of 0.2-7, and typically diluted with a solvent or a solvent mixture, most typically ethanol) is applied to the polymer substrate surface in one or more steps (in particular in one step). In particular, both application steps (the priming step and step (iii)) involve dipping of the substrate polymer surface in the primer solution and polymer solution, respectively. More preferred, the priming step and step (iii) are each performed by one dip of the substrate polymer surface (or the relevant part thereof) into the relevant solution (i.e. the primer solution and the polymer solution, respectively).

Step (iv)

After application of the polymer solution to the substrate polymer surface, any solvent or at least a part thereof is evaporated from the polymer solution present on said substrate polymer surface. The aim is to remove the most volatile components of the vehicle. The volatile components may be removed by passive evaporation, by leading a stream of air over the surface of the substrate polymer, or by applying a reduced pressure over the surface of the substrate polymer. The drying typically takes place at a temperature in the range of 20-100° C. for 1-60 minutes, such as at 70° C. for 30 minutes. Furthermore, it may be necessary or desirable to increase the temperature of the substrate polymer or the air surrounding the substrate polymer to speed up the evaporation process. Preferably, the evaporation process is facilitated by drying the substrate polymer with the polymer solution at a temperature in the range of 25-100° C. depending on the thermostability of the substrate polymer. Typically, the substrate polymer (e.g. a medical device) is dried in an oven.

Although the curing of the hydrophilic polymer of the polymer solution may be effected or at least initiated upon the at least partial evaporation of the solvent, it is often desirable to specifically induce curing (cross-linking) of the hydrophilic polymer. Most advantageously, the free-radical curing (and cross-linking) is performed by application of radiation, e.g. UV radiation. The method of curing, in particular the frequency of the UV light, is depending on the choice of photoinitiator. The person skilled in the art will know the means and procedures necessary for efficient curing, see e.g. "Radiation Curing in Polymer Science and Technology", volumes. I-IV, eds. J. P. Fouassler and J. F. Rabek, Elsevier, London, 1993.

In the present context, the terms "cross-linked" and "cured" when referring to a polymer or polymers are intended to mean attachment of two chains of polymer molecules by covalent chemical bonds, possibly through a linker. "Cross-linked" and "cured" in particular means that such covalent chemical bonds occur between chains of similar nature.

In a preferred embodiment of the above method, the hydrophilic coating is prepared by dipping a medical device having a substrate polymer surface of polyurethane in a solution of the preferred hydrophilic polymer (i.e. polyvinyl pyrrolidone), a photoinitiator, one or more plasticizers selected from acetyl triethyl citrate, dimethyl sulfone, ethylene carbonate, glycerol diacetate, glycerol triacetate, hexamethylphosphoramide, isophorone, methyl salicylate, N-acetyl morpholine, propylene carbonate, quinoline, sulfolane, triethyl citrate, and triethyl phosphate, and one or more solvents selected from ethanol, N-methyl-2-pyrrolidone, dimethyl sulfoxide, acetone, 1,3-dioxolane and dimethyl formamide. The device is subsequently dried in an oven at a temperature of 25-100° C., typically for 5-60 minutes, so as to remove a substantial portion of the solvent and radiated with specific ultraviolet light to effect cross-linking.

The present invention thus also provides a medical device comprising a substrate polymer surface having thereon a cross-linked hydrophilic coating of a hydrophilic polymer, said medical device being obtainable by the method defined herein.

The cross-linked hydrophilic coatings thus obtained constitute an important aspect of the invention. Thus, the invention further provides a medical device comprising a hydrophilic coating of a cross-linked hydrophilic polymer, said coating comprising a hydrophilic plasticizer having a solubility in water of at least 6 g/L, a boiling point above 210° C. at 760 mmHg, and a Hansen $\delta_H$ parameter of less than 20. Embodiments of the medical device including the hydrophilic coating, the hydrophilic polymer, the hydrophilic plasticizer, etc. follow the description given herein with respect to the method of the invention. The coatings are preferably prepared according to the above method, but may alternatively be prepared in a somewhat different manner.

The hydrophilic coatings are highly lubricious when wet as the coatings take up a significant amount of water, which leaves a non-bonded layer of free water molecules at the surface of the coating. The non-bonding character of the surface water is believed to cause the low friction of the wet coating. Hence, the coating when applied to a biomedical or other device will improve biocompatibility and patient compliance. However, for most applications there will be high demands to the internal and the bonding strength for the coating.

Examples of medical devices on which the cross-linked hydrophilic coating can be applied are catheters, endoscopes and laryngoscopes, tubes for feeding or drainage or endotracheal use, guide wires, wound dressings, implants, extracorporeal blood conduits, membranes e.g. for dialysis, blood filters, devices for circulatory assistance, etc. Particularly relevant medical devices are catheters and guide wires.

A still further aspect of the present invention is the use of a polymer solution for the preparation of a cross-linked hydrophilic coating, said polymer solution comprising 1-20% by weight of a hydrophilic polymer, 0-5% by weight of additive(s), and a vehicle with plasticizing effect on the hydrophilic polymer, said vehicle comprising at least one plasticizer having a solubility in water of at least 6 g/L, a boiling point above 210° C. at 760 mmHg, and a Hansen $\delta_H$ parameter of less than 20. This use may be fairly general and applicable for a wide range of substrates. One should, however, preferably take into account the recommendations given above with respect to the selection of a substrate, the hydrophilic polymer, the vehicle, etc.

In one embodiment, the polymer solution consists of:
1-20% by weight of the hydrophilic polymer,
0-5% by weight of additive(s),
1-40% by weight of plasticizer(s), and
50-95% by weight of solvent(s).

In a more particular embodiment, the polymer solution consists of:
1-20% by weight of polyvinyl pyrrolidone as the hydrophilic polymer,
0-5% by weight of additive(s),
1-40% by weight of plasticizer(s) selected from acetyl triethyl citrate, dimethyl sulfone, ethylene carbonate, glycerol diacetate, glycerol triacetate, hexamethylphosphoramide, isophorone, methyl salicylate, N-acetyl morpholine, propylene carbonate, quinoline, sulfolane, triethyl citrate, and triethyl phosphate, and
50-95% by weight of solvents selected from ethanol, N-methyl-2-pyrrolidone, dimethyl sulfoxide, acetone, 1,3-dioxolane and dimethyl formamide.

The invention is further illustrated by means of the following examples.

EXPERIMENTALS

All quantities indicated herein as "parts" refer to parts by weight.

Materials

PVP K-90 (molecular weight $1.2 \times 10^6$ g/mol) was obtained from ISP Technologies.

The UV catalyst Esacure® KIP 150 was obtained from Lamberti SpA.

Bis(2-ethylhexyl)phthalate (dioctyl phthalate, DOP), dimethyl formamide (DMF), dimethyl sulfoxide (DMSO), and N-methyl-2-pyrrolidone were obtained from Merck.

Acetyl tributyl citrate (Citrofol BII), acetyl triethyl citrate (Citrofol AII), tributyl citrate (Citrofol BI), and triethyl citrate (Citrofol AI) were obtained from Jungbunzlauer.

Glycerol diacetate was obtained from Unichema International.

Glycerol triacetate was obtained from Unichema International or Merck.

Camphor, castor oil, dibutyl sebacate and sulfolane were obtained from Aldrich.

Dibutyl phthalate was obtained from BASF.

1,3-Dioxolane and triethyl phosphate were obtained from Fluka.

Examples 1-13

Preparation of Coatings with 8.7% Plasticizer 5 parts polyvinyl pyrrolidone (PVP) K-90 and 0.024 parts Esacuree KIP 150 were dissolved in 82 parts ethanol, 4.35 parts N-methyl-2-pyrrolidone (NMP), and 8.7 parts plasticizer according to Table 2 and magnetically stirred overnight. The coating was applied to polyurethane catheters by dipping the catheters in the polymer solution at room temperature and withdrawing them at a speed of 21 mm/s. The catheters were dried for 30 minutes at 70° C. and then UV cured for 150 seconds at 40-50° C. The UV cured catheters were immediately rubbed vigorously between the fingers under running water in order to evaluate whether the coating was stable and lubricious. They were then stored in water for at least 72 hours, and vigorous finger rubbing under running water was repeated. The catheters were then scored "stable" and "lubricious" only if the coating was still stable and lubricious at this time. The result of the test is seen in Table 2.

TABLE 2

Performance of coatings with 8.7% of various plasticizers

| Example no. | % PVP K-90 | % Esacure KIP 150 | % ethanol | % NMP | 8.7% plasticiser | Coating stable? | Coating lubricious? |
|---|---|---|---|---|---|---|---|
| 1 | 5 | 0.024 | 82 | 4.35 | Acetyl triethyl citrate (Citrofol AII) | Yes | Yes |
| 2 | 5 | 0.024 | 82 | 4.35 | Glycerol diacetate | Yes | Yes |
| 3 | 5 | 0.024 | 82 | 4.35 | Glycerol triacetate | Yes | Yes |
| 4 | 5 | 0.024 | 82 | 4.35 | Triethyl citrate (Citrofol AI) | Yes | Yes |
| 5 | 5 | 0.024 | 82 | 4.35 | Glycerol | No | Yes |
| 6 | 5 | 0.024 | 82 | 4.35 | Acetyl tributyl citrate (Citrofol BII) | No | No |
| 7 | 5 | 0.024 | 82 | 4.35 | Camphor | No | No |
| 8 | 5 | 0.024 | 82 | 4.35 | Castor oil | No | No |
| 9 | 5 | 0.024 | 82 | 4.35 | Dibutyl phthalate | No | No |
| 10 | 5 | 0.024 | 82 | 4.35 | Dibutyl sebacate | No | No |
| 11 | 5 | 0.024 | 82 | 4.35 | Dioctyl adipate (DOA) | Somewhat | No |
| 12 | 5 | 0.024 | 82 | 4.35 | Dioctyl phthalate (DOP) | No | No |
| 13 | 5 | 0.024 | 82 | 4.35 | Tributyl citrate (Citrofol BI) | No | No |

Acetyl triethyl citrate, glycerol diacetate, glycerol triacetate and triethyl citrate gave both stable and lubricious coatings. However, glycerol gave a lubricious coating which was not stable. The rest of the plasticizers gave a coating that was neither stable nor lubricious.

Examples 14-17

Preparation of Coatings with 10% Triethyl Citrate, 5% NMP and 79.0% of Various Solvents 6 parts PVP K-90 and 0.03 parts Esacure® KIP 150 were dissolved in 78.97 parts solvent, 5 parts NMP, and 10 parts triethyl citrate according to Table 3 and magnetically stirred overnight. The coating was applied to polyurethane catheters and UV cured as described in Examples 1-13. The resulting coatings were stable and lubricious. The result of the test is seen in Table 3.

TABLE 3

Performance of coatings with 10% triethyl citrate as plasticizer and 79.0% solvent

| Example no. | % PVP K-90 | % Esacure KIP 150 | 79.0% solvent | % NMP | % triethyl citrate | Coating stable? | Coating lubricious? |
|---|---|---|---|---|---|---|---|
| 14 | 6 | 0.03 | Ethanol | 5 | 10 | Yes | Yes |
| 15 | 6 | 0.03 | Acetone | 5 | 10 | Almost | Yes |
| 16 | 6 | 0.03 | Dimethyl formamide | 5 | 10 | Yes | Yes |
| 17 | 6 | 0.03 | 1,3-Dioxolane | 5 | 10 | Yes | Yes |

Ethanol, dimethyl formamide and 1,3-dioxolane all gave coatings that were stable and lubricious when wet. Acetone gave a coating that was lubricious and stable during vigorous finger rubbing under running water immediately after UV curing. After at least 72 hours storage in water and repeated challenge by finger rubbing under running water, the acetone coating was lubricious but slightly unstable. However, the acetone coating was superior to those produced in Examples 5-13. These examples show that the hydrophilic plasticizers can produce stable, lubricious coatings with a variety of solvents.

Example 18

Preparation of a Coating with 10% Triethyl Citrate, 79.0% Ethanol and 5% Dimethyl Sulfoxide 6 parts PVP K-90 and 0.03 parts Esacure® KIP 150 were dissolved in 78.97 parts ethanol, 5 parts dimethyl sulfoxide (DMSO), and 10 parts triethyl citrate and magnetically stirred overnight. The coating was applied to polyurethane catheters and UV cured as described in Examples 1-13. The resulting coating was lubricious and stable during vigorous finger rubbing under running water immediately after UV curing. After at least 72 hours storage in water and repeated challenge by finger rubbing under running water, the coating was lubricious but slightly unstable. However, the coating was superior to those produced in Examples 5-13. Hence, a coating of good quality resulted when N-methyl-pyrrolidone was replaced by DMSO in the coating recipe.

Example 19

Preparation of a Coating with 20% Sulfolane and 73.97% Ethanol 6 parts PVP K-90 and 0.03 parts Esacure® KIP 150 were dissolved in 73.97 parts ethanol and 20 parts sulfolane and magnetically stirred overnight. The coating was applied to polyurethane catheters and UV cured as described in Examples 1-13. The resulting coating was lubricious and stable during vigorous finger rubbing under running water after UV curing. After repeated challenges by finger rubbing under running water after 4 months storage in water, the coating was still very lubricious and completely stable. Hence, a coating of superior quality resulted when sulfolane was present as the plasticizer together with ethanol as the volatile solvent in the vehicle.

Example 20

Preparation of a Coating with 20% Sulfolane and 73.97% Acetone 6 parts PVP K-90 and 0.03 parts Esacure® KIP 150 were dissolved in 73.97 parts acetone and 20 parts sulfolane and magnetically stirred overnight. The coating was applied to polyurethane catheters and UV cured as in Examples 1-13. The resulting coating was lubricious and stable during vigorous finger rubbing under running water after UV curing. After 12 days storage in water, the coating was stable but somewhat less lubricious than right after manufacture. After 4 months storage in water and repeated challenge by finger rubbing under running water, the coating was unstable. However, the coating was superior to those produced in Examples 5-13. Hence, a coating of good quality resulted when sulfolane was present as the plasticizer together with acetone as the volatile solvent in the vehicle.

Example 21

Preparation of a Coating with 20% Triethyl Phosphate and 73.97% Ethanol 6 parts PVP K-90 and 0.03 parts Esacure® KIP 150 were dissolved in 73.97 parts ethanol and 20 parts triethyl phosphate and magnetically stirred overnight. The coating was applied to polyurethane catheters and UV cured as in Examples 1-13. The resulting coating was almost stable and somewhat lubricious during vigorous finger rubbing under running water after UV curing. After 2 days in water, the coating was rough and quite unstable but still better than those produced in Examples 5-13. Hence, a coating of reasonable quality resulted when triethyl phosphate was present as the plasticizer together with ethanol as the volatile solvent in the vehicle.

The invention claimed is:

1. A method for the preparation of a cross-linked hydrophilic coating of a hydrophilic polymer on a substrate polymer surface of a medical device, said method comprising the steps of:
(i) providing a medical device having a substrate polymer surface;
(ii) providing a polymer solution comprising 1-20% by weight of a hydrophilic polymer, 0-5% by weight of additive(s), and the balance of said solution being a vehicle having at least one plasticizer with a solubility in water of at least 6 g/L, a boiling point above 210° C. at 760 mmHg, and a Hansen δH parameter of less than 20 wherein the plasticizer is selected from the group consisting of dimethyl sulfone, ethylene carbonate, glycerol diacetate, glycerol triacetate, hexomethylphosphoramide, isophorone, methyl salicylate, N-acetyl morpholine, propylene carbonate, quinoline, sulfolane, and triethyl phosphate;
(iii) applying said polymer solution to said substrate polymer surface;
(iv) evaporating at least a part of the vehicle from said polymer solution present on said substrate polymer surface at a temperature of 25°-100° C.; and
(v) curing said hydrophilic polymer without rewetting the medical device, wherein said curing occurs by irradiation and is the only irradiation step in the process.

2. The method according to claim 1, wherein the polymer solution is applied to said substrate polymer surface in a single application step.

3. The method according to claim 1, wherein the vehicle comprises at least one solvent.

4. The method according to claim 3, wherein the polymer solution consists of 1-20% by weight of the hydrophilic polymer, 0-5% by weight of additive(s), 1-40% by weight of plasticizer(s), and 50-95% by weight of solvent(s).

5. The method according to claim 1, wherein the substrate polymer is polyurethane.

6. The method according to claim 1, wherein the hydrophilic polymer is polyvinyl pyrrolidone.

7. A medical device comprising a substrate polymer surface having thereon a cross-linked hydrophilic coating of a hydrophilic polymer, said medical device being obtained by the method of claim 1.

8. A medical device comprising a hydrophilic coating of a cross-linked hydrophilic polymer, said coating having a hydrophilic plasticizer with a solubility in water of at least 6 g/L, a boiling point above 210° C. at 760 mmHg, and a Hansen δH parameter of less than 20, said medical device being prepared according to the method of claim 1.

9. A method of use of a polymer solution for the preparation of a cross-linked hydrophilic coating, wherein said polymer solution includes 1-20% by weight of a hydrophilic polymer, 0-5% by weight of additive(s), and the balance of said solution being a vehicle having a plasticizing effect on the hydrophilic polymer and including at least one plasticizer having a solubility in water of at least 6 g/L, a boiling point above 210° C. at 760 mmHg, and a Hansen δH parameter of less than 20 wherein the plasticizer is selected from the group consisting of dimethyl sulfone, ethylene carbonate, glycerol diacetate, glycerol triacetate, hexamethylphosophoramide, isophorone, methyl salicylate, N-acetyl morpholine, propylene carbonate, quinoline, sulfolane, and triethyl phosphate, said method comprising the steps of:
(a) applying said polymer solution to said substrate polymer surface;
(b) evaporating at least a part of the vehicle from said polymer solution present on said substrate polymer surface at a temperature of 25°-100° C.; and curing said hydrophilic polymer by irradiation without rewetting the medical device,
wherein said method includes only a single irradiation step.

10. The method according to claim 5, wherein the hydrophilic polymer is polyvinyl pyrrolidone.

11. A method for the preparation of a cross-linked hydrophilic coating of a hydrophilic polymer on a substrate polymer surface of a medical device, said method consisting of the steps of:
(i) providing a medical device having a substrate polymer surface;
(ii) providing a polymer solution having 1-20% by weight of a hydrophilic polymer, 0-5% by weight of additive(s), and the balance of said solution being a vehicle having at least one plasticizer with a solubility in water of at least 6 g/L, a boiling point above 210° C. at 760 mmHg, and a Hansen δH parameter of less than 20 wherein the plasticizer is selected from the group consisting of dimethyl sulfone, ethylene carbonate, glycerol diacetate, glycerol triacetate, hexamethylphosphoramide, isophorone, methyl salicylate, N-acetyl morpholine, propylene carbonate, quinoline sulfolane, and triethyl phosphate;

(iii) applying said polymer solution to said substrate polymer surface;

(iv) evaporating at least a part of the vehicle from said polymer solution present on said substrate polymer surface at a temperature of 25°-100° C.; and (v) curing said hydrophilic polymer.

12. The method according to claim 11, wherein the polymer solution is applied to said substrate polymer surface in one single application step.

13. The method according to claim 11, wherein the vehicle comprises at least one solvent.

14. The method according to claim 13, wherein the polymer solution consists of 1-20% by weight of the hydrophilic polymer, 0-5% by weight of additive(s), 1-40% by weight of plasticizer(s), and 50-95% by weight of solvent(s).

15. The method according to claim 11, wherein the substrate polymer is polyurethane.

16. The method according to claim 11, wherein the hydrophilic polymer is polyvinyl pyrrolidone.

17. A medical device comprising a substrate polymer surface having thereon a cross-linked hydrophilic coating of a hydrophilic polymer, said medical device being obtained by the method of claim 11.

18. A medical device comprising a hydrophilic coating of a cross-linked hydrophilic polymer, said coating having a hydrophilic plasticizer with a solubility in water of at least 6 g/L, a boiling point above 210° C. at 760 mmHg, and a Hansen δH parameter of less than 20, said medical device being prepared according to the method of claim 11.

19. A method of use of a polymer solution for the preparation of a cross-linked hydrophilic coating, wherein said polymer solution includes 1-20% by weight of a hydrophilic polymer, 0-5% by weight of additive(s), and the balance of said solution being a vehicle having a plasticizing effect on the hydrophilic polymer and including at least one plasticizer having a solubility in water of at least 6 g/L, a boiling point above 210° C. at 760 mmHg, and a Hansen δH parameter of less than 20 wherein the plasticizer is selected from the group consisting of dimethyl sulfone, ethylene carbonate, glycerol diacetate, glycerol triacetate, hexamethylphosphoramide, isophorone, methyl salicylate, N-acetyl morpholine, propylene carbonate, quinoline, sulfolane, and triethyl phosphate, said method consisting of the steps of:

(a) applying said polymer solution to said substrate polymer surface;

(b) evaporating at least a part of the vehicle from said polymer solution present on said substrate polymer surface at a temperature of 25°-100° C.; and curing said hydrophilic polymer by irradiation, wherein said method includes only a single irradiation step.

20. The method according to claim 15, wherein the hydrophilic polymer is polyvinyl pyrrolidone.

21. The method according to claim 1, wherein evaporating at least part of said vehicle takes place at a temperature of 70°-100° C.

22. The method according to claim 9, wherein evaporating at least part of said vehicle takes place at a temperature of 70°-100° C.

23. The method according to claim 11, wherein evaporating at least part of said vehicle takes place at a temperature of 70°-100° C.

* * * * *

UNITED STATES PATENT AND TRADEMARK OFFICE
CERTIFICATE OF CORRECTION

PATENT NO. : 8,728,508 B2  
APPLICATION NO. : 10/540108  
DATED : May 20, 2014  
INVENTOR(S) : Nielsen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1213 days.

Signed and Sealed this
Twenty-eighth Day of July, 2015

Michelle K. Lee
*Director of the United States Patent and Trademark Office*